US00PP14927P2

(12) United States Plant Patent
Strope

(10) Patent No.: US PP14,927 P2
(45) Date of Patent: Jun. 22, 2004

(54) PETUNIA PLANT NAMED 'BALRUFROSE'

(50) Latin Name: *Petunia×hybrida*
Varietal Denomination: Balrufrose

(75) Inventor: Kerry M. Strope, Pismo Beach, CA (US)

(73) Assignee: Ball Floraplant, a division of Ball Horticultural Co., West Chicago, IL (US)

( * ) Notice: Subject to any disclaimer, the term of this patent is extended or adjusted under 35 U.S.C. 154(b) by 60 days.

(21) Appl. No.: 10/107,589

(22) Filed: Mar. 26, 2002

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—Michelle Kizilkaya
(74) *Attorney, Agent, or Firm*—Wood, Phillips, Katz, Clark & Mortimer

(57) ABSTRACT

A new and distinct Petunia plant named 'Balrufrose', characterized by its fully double, rose colored flowers, mounded-trailing habit and dark green leaves.

1 Drawing Sheet

Latin name of the genus and species of plant claimed: *Petunia×hybrida.*
Variety Denomination: 'Balrufrose'.

BACKGROUND OF THE INVENTION

The present invention comprises a new and distinct Double Petunia plant, botanically known as *Petunia×hybrida*, and hereinafter referred to by the cultivar name 'Balrufrose'.

'Balrufrose' is the result of a planned breeding program with the objective of developing Petunia cultivars with large, double flowers and vigorous mounded trailing growth habits.

The female parent of 'Balrufrose' was the proprietary *Petunia×hybrida* variety, designated 'BFP-10' (Trialing Pink), which exhibits a vigorous trailing habit, dark green foliage and single pink flowers. The male parent of 'Balrufrose' was the propriety *Petunia×hybrida* variety, designated '30251-1', which exhibits medium vigor, mounded trailing habit, dark green foliage and double coral flowers. The new cultivar was discovered and selected as a single seeding originating from within the progeny of the above stated cross during September 1998 in a controlled environment at Arroyo Grande, Calif. and initially designated 'BFP-672' and subsequently named 'Balrufrose'.

Asexual reproduction of the new cultivar has been carried out at Arroyo Grande, Calif. and West Chicago, Ill. by terminal tip cuttings and has demonstrated that the unique characteristics of the new cultivar as herein described are firmly fixed and retained through successive generations of such asexual propagation.

SUMMARY OF THE INVENTION

It was found that the cultivar of the present invention:

(a) exhibits fully double, bright rose colored flowers;

(b) forms a dark green foliage;

(c) exhibits a good basal branching character; and (d) exhibits a mounded trailing growth habit.

The new cultivar of the present invention can be compared to Petunia plant named 'Cobink' (U.S. Plant Pat. No. 12,012). However, in side-by-side comparisons, plants of the new cultivar are more floriferous, exhibit smaller leaves and shorter internodes than 'Cobink'. The flowers of 'Balrufrose' have more petals and are darker in color than those of 'Cobink'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 12 weeks in a greenhouse at West Chicago, Ill., U.S.A.

DETAILED BOTANICAL DESCRIPTION

The cultivar 'Balrufrose' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Oct. 15, 2001. The readings were taken between 1:00 and 3:00 p.m. under natural daylight conditions.

Plants used for the following descriptions and measurements were grown in 10 cm pots for 12 weeks from rooted cuttings. The plants were produced from cuttings taken from stock plants and grown in a double polycarbonate covered greenhouse under conditions comparable to those used in commercial practice. A soilless growth medium was utilized while temperatures of approximately 55° to 75° F. (13° to 24° C.) during the day and approximately 50° to 60° F. (10° to 16° C.) during the night and light levels of 5,000 to 8,000 footcandles were maintained.

Classification:

*Botanical.*—*Petunia×hybrida* cultivar 'Balrufrose'.

Parentage:

*Female parent.*—Proprietary *Petunia×hybrida* variety designated 'BFP-10' (Trailing Pink).

*Male parent.*—Proprietary *Petunia×hybrida* variety designated '30251-1'.

Propagation:

*Type cutting.*—Terminal tip.

*Time to initiate roots.*—Approximately 7 to 10 days.

*Time to develop roots.*—Approximately 21 to 30 days.

*Root description.*—Fibrous, branching.

Plant description:

*Crop time.*—Approximately 6 to 8 weeks are required to produce a finished plant from a rooted cutting under long day conditions.

*Habit of growth.*—Moderately vigorous with good basal branching. Pinching improves basal branching.

*Form.*—Mounded trailing.

*Plant height.*—A mature plant, 12 weeks after the planting of a rooted cuttings, commonly measures approximately 16.6 cm from the soilline to the top of the plant plane.

*Plant spread.*—Approximately 35.8 cm.

*Lateral branches.*—An average of 3.3 branches per plant, approximately 26.2 cm in length and 3 mm in diameter, densely pubescent and 144A in color. Internode length at the middle of the branch is approximately 1.6 cm.

*Foliage.*—Leaves are non-fragrant, single, arrangement is alternate along the stem becoming opposite at the base of the peduncle. Leaves are at an acute angle to the stem, ovate with entire margin, acute apex and attenuate base. Upper surface is densely pubescent, lower surface is moderately pubescent and margin is densely pubescent. There are approximately 14 leaves per branch. Leaf length is approximately 3.6 cm and width is approximately 2.2 cm. The upper surface of young foliage is closest to 144A and the lower surface is closest to 144B. The upper surface of mature foliage is closest to 146A and the lower surface is closest to 146C. Both upper and lower surfaces have pinnate venation closest to 144C. The petiole length is approximately 3 mm, the diameter is approximately 2 mm and the color is closest to 144C.

Flowering description:

*Flowering habit.*—Freely flowering.

*Natural flowering season.*—Year round in greenhouse environment and spring through fall in outdoor garden.

*Lastingness of the bloom.*—Bloom remains open for approximately 5–7 days.

Flower description:

*Type.*—Double, solitary, axillary, salverform, with pungent fragrance. Flowers are persistent.

*Size.*—Length (height) is approximately 4.4 cm and width is approximately 5.8 cm.

*Corolla.*—Twenty-two (22) obovate petals with the outer whorl of five petals fused to form corolla tube. All petals have cuspidate apex, entire ruffled margin and smooth texture. Petal length from throat is 2.4 cm and width at widest point is 2.2 cm. Color of margin of upper surface of petals is 74B with venation of 74A. The middle of the upper surface is 74A. Color of lower surface of petals is 78C with midveins of 144C.

*Corolla tube.*—Length is approximately 2 cm, diameter at distal end is approximately 5 mm and diameter at proximal end is approximately 1.5 cm. Color of outer surface is 155A with veins of 144C and color of inner surface is 155D with veins of 144C. Outer surface of tube is moderately pubescent, inner surface is smooth.

*Peduncle.*—Strong, densely pubescent, at an acute angle to the stem, approximately 1.3 cm in length and 2 mm in diameter. Peduncle color is 144A.

*Sepals.*—Five, non-imbricate, approximately 1.7 cm in length and 4 mm in diameter, linear in shape with broadly acute to rounded apex and entire margin. Both surfaces are densely pubescent. The color of the upper surface is 144A and the lower surface is 144B.

*Flower bud.*—Ovate, elongating as it matures. At first color the bud is approximately 2.9 cm in length and 1.4 cm in diameter. Bud color is 77B.

*Reproductive organs.*—There may be as many as 21 stamens. Anther shape is oval and 3 mm in length. Pollen is abundant and color is 159C. Other reproductive organs are generally malformed and not distinguishable. However, occasional functional pistils can be identified.

Seed production: Limited seed production. Seed Description: Quantity: numerous; shape: spherical; texture: smooth; color: 200A; size: less than 1 millimeter.

Disease resistance: Exhibits resistance to tobamovirus infection.

I claim:

1. A new and distinct cultivar of Petunia plant named 'Balrufrose' substantially as herein shown and described, which:

(a) exhibits fully double, rose colored flowers;

(b) dark green foliage;

(c) a good basal branching character; and (d) a mounded trailing growth habit.

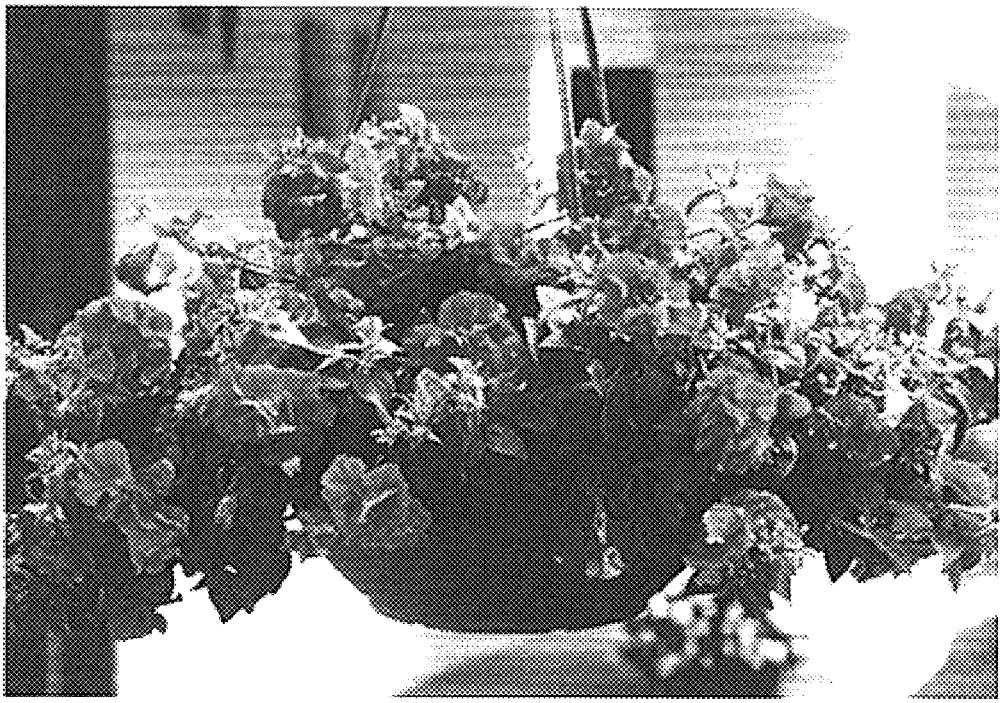

* * * * *